US008415167B2

(12) United States Patent
Kodama et al.

(10) Patent No.: US 8,415,167 B2
(45) Date of Patent: Apr. 9, 2013

(54) OXYGEN DETECTOR AND METHOD FOR MANUFACTURING OXYGEN DETECTOR

(75) Inventors: Ryuichi Kodama, Kashiwa (JP); Mitsuyuki Sato, Takahagi (JP)

(73) Assignee: Powdertech Co., Ltd., Chiba (JP)

(*) Notice: Subject to any disclaimer, the term of this patent is extended or adjusted under 35 U.S.C. 154(b) by 157 days.

(21) Appl. No.: 12/907,260

(22) Filed: Oct. 19, 2010

(65) Prior Publication Data

US 2011/0097811 A1   Apr. 28, 2011

(30) Foreign Application Priority Data

Oct. 28, 2009   (JP) .................................. 2009-247281

(51) Int. Cl.
*G01N 33/00* (2006.01)
*G01N 21/25* (2006.01)

(52) U.S. Cl. ........ 436/138; 422/400; 422/420; 422/425; 422/430; 436/127; 436/136; 436/164; 436/166

(58) Field of Classification Search .................. 422/400, 422/420, 425, 430; 436/127, 136, 138, 164, 436/166

See application file for complete search history.

(56) References Cited

U.S. PATENT DOCUMENTS

| | | | | |
|---|---|---|---|---|
| 2,170,596 | A | * | 8/1939 | Quiggle .......................... 423/219 |
| 2,967,092 | A | * | 1/1961 | Buchoff et al. ................. 436/138 |
| 4,169,811 | A | * | 10/1979 | Yoshikawa et al. ............ 436/138 |
| 4,349,509 | A | * | 9/1982 | Yoshikawa et al. ............ 422/426 |
| 4,814,267 | A | * | 3/1989 | Zeikus et al. ..................... 435/95 |
| 5,096,813 | A | * | 3/1992 | Krumhar et al. ................. 435/28 |
| 5,358,876 | A | * | 10/1994 | Inoue et al. ..................... 436/136 |
| 6,676,901 | B1 | * | 1/2004 | Hatakeyama et al. .......... 422/416 |
| 6,703,245 | B2 | * | 3/2004 | Sumitani et al. ............... 436/136 |
| 7,921,798 | B2 | * | 4/2011 | Kodama et al. ................. 116/206 |
| 8,114,673 | B2 | * | 2/2012 | Mills et al. ........................ 436/77 |
| 2003/0082823 | A1 | * | 5/2003 | Sumitani et al. ............... 436/136 |
| 2004/0258562 | A1 | * | 12/2004 | Mills et al. ........................ 422/57 |
| 2006/0141106 | A1 | * | 6/2006 | Kodama et al. ................. 426/231 |
| 2008/0070307 | A1 | * | 3/2008 | Kodama ............................. 436/2 |
| 2009/0223432 | A1 | * | 9/2009 | Kodama et al. ................. 116/206 |

FOREIGN PATENT DOCUMENTS

| | | | |
|---|---|---|---|
| JP | 55-99070 | * | 7/1980 |
| JP | 56-42138 | * | 4/1981 |
| JP | 56-65072 | * | 6/1981 |
| JP | 56-84772 | * | 7/1981 |
| JP | 56-108955 | * | 8/1981 |
| JP | 58-182555 | * | 10/1983 |
| JP | 59-19855 | * | 2/1984 |
| JP | 59-65764 | * | 4/1984 |
| JP | 60-80763 | * | 5/1985 |
| JP | 61-152299 | * | 7/1986 |
| JP | 61-212760 | * | 9/1986 |
| JP | 2-57975 | * | 2/1990 |
| JP | 2-173566 | * | 7/1990 |
| JP | 4-83533 | * | 3/1992 |
| JP | 5-312799 | * | 11/1993 |
| JP | 6-222050 | * | 8/1994 |
| JP | 6-230004 | * | 8/1994 |
| JP | 7-63746 | * | 3/1995 |
| JP | 2580157 | | 11/1996 |
| JP | 2007-3259 | | 1/2007 |
| JP | 2009-74992 | * | 4/2009 |

* cited by examiner

*Primary Examiner* — Arlen Soderquist

(74) *Attorney, Agent, or Firm* — Greenblum & Bernstein, P.L.C.

(57) ABSTRACT

It is an object of the present invention to provide: an oxygen indicator aqueous solution for an oxygen detector that has high heat resistance, can be stored at room temperature, and can maintain an excellent ability to detect oxygen, regardless of the atmospheric temperature; an oxygen detector; and a method for manufacturing an oxygen detector.

In order to achieve this object, there is provided an oxygen indicator aqueous solution for an oxygen detector that is an aqueous solution comprising reducing saccharides, a basic substance, and a redox dye reduced by the reducing saccharides, the aqueous solution comprising, as the reducing saccharides, a monosaccharide as a first component and a reducing trisaccharide as a second component. In addition, there is provided a manufacturing method preferred for the manufacturing of the oxygen detector.

14 Claims, No Drawings

OXYGEN DETECTOR AND METHOD FOR MANUFACTURING OXYGEN DETECTOR

BACKGROUND OF THE INVENTION

1. Field of the Invention

The present invention relates to an oxygen detector in which a change in the amount of oxygen in an atmosphere is made visible by a change in color, and a method for manufacturing an oxygen detector.

2. Description of the Related Art

In the storage of food, medicine, or the like, oxygen in the atmosphere oxidizes the food, the medicine, or the like and decreases the quality of the food, the medicine, or the like. Then, in order to prevent the decrease in quality during storage, the food, the medicine, or the like is placed, together with a deoxidizer, in a packaging container (including a packaging bag) and hermetically packaged. Oxygen in the packaging container can be absorbed by the deoxidizer or the like, and the food, the medicine, or the like can be stored in an oxygen-free state (for example, an oxygen concentration of 0.1% or less).

In recent years, an oxygen detector has been enclosed in a packaging container, together with a deoxidizer. The oxygen detector has been used to detect the presence or absence of oxygen in the packaging container. The presence or absence of oxygen in a hermetic packaging container is made visible by a change in color of the oxygen detector. The user can easily check whether food, medicine, or the like is stored in an oxygen-free state or not, based on the color of the oxygen detector.

This type of oxygen detector generally comprises a reducing saccharide, a basic substance, and a redox dye which has the ability of change color depending on its oxidative state (for example, Japanese Patent: Japanese Patent No. 2580157 B2, and Japanese Patent Application: Japanese Patent Laid-Open No. 2007-3259 A1). The reducing saccharide is used to maintain the redox dye in the reduced state when the atmosphere is in an oxygen-free state. When the redox dye maintained in the reduced state is oxidized by oxygen in the atmosphere, the redox dye changes the color. In this manner, the oxygen detector detects oxygen, using a mechanism of changing color of the redox dye depends on its oxidative state. Therefore, a clear color change and a quick color change response accompanying a change in the amount of oxygen in the atmosphere are required of the oxygen detector. Then, in the above Patent Documents, a change in color caused by the oxygen detector between the reduced state and the oxidized state is made clearer, using a dye not reduced by the reducing saccharide, such as a red food coloring.

The oxygen detector is manufactured by preparing an oxygen indicator aqueous solution (oxygen detecting solution) for an oxygen detector comprising a reducing saccharide, a basic substance, and a redox dye and allowing this oxygen indicator aqueous solution to be carried on various carriers, such as a sheet-shaped carrier and a tablet. The reducing saccharide is ring-opened in the oxygen indicator aqueous solution adjusted to be basic by the basic substance and forms a chain structure having a reducing group (an aldehyde group or a ketone group), which reduces the redox dye. Conventionally, monosaccharides having large reducing power, such as D-glucose, have been mainly used as such a reducing saccharide.

However, conventional problems are that the oxygen detector has low heat resistance. That is, when the oxygen detector is stored at high temperature (for example, a temperature equal to or higher than room temperature, 35° C.), the ability to detect oxygen decreases. Therefore, a quick color change response is not obtained and a color tone change is unclear when the amount of oxygen in the atmosphere changes.

A cause of the decrease in the ability to detect oxygen during storage at high temperature is the browning of the reducing saccharide. The browning of the reducing saccharide is caused by the fact that the reducing saccharide forming the chain structure in the aqueous solution reacts with the basic substance and is decomposed from an end having the reducing group. This browning of the reducing saccharide tends to occur as the atmospheric temperature increases. Particularly, monosaccharides have large reducing power and high reactivity, and therefore, browning tends to occur. When the reducing saccharide browns in the oxygen indicator aqueous solution, the color of the oxygen detector also turns brown, and therefore, a color change is unclear. In addition, when the reducing groups are consumed due to the progress of the reaction with the basic substance, it is difficult to maintain the redox dye in the reduced state in an oxygen-free state, and part of the redox dye may have an oxidized structure. In this case, the ability to detect oxygen decreases, and even if oxygen is detected, a color change may be unclear, and a quick color change response may not be obtained. Therefore, conventionally, by storing the oxygen detector at low temperature (for example, 10° C. or less) before shipment, the browning of the reducing saccharide has been prevented to prevent degradation in the ability of the oxygen detector to detect oxygen.

Then, it is an object of the present invention to provide an oxygen detector that has high heat resistance, can be stored at room temperature, and can maintain an excellent ability to detect oxygen, regardless of the atmospheric temperature, and a method for manufacturing an oxygen detector.

SUMMARY OF THE INVENTION

As a result of diligent study, the present inventors have achieved the above object by using the following oxygen detector and method for manufacturing an oxygen detector.

An oxygen detector according to the present invention is an oxygen detector comprising an oxygen indicator aqueous solution comprising reducing saccharides, a basic substance, and a redox dye reduced by the reducing saccharides, carried on a carrier, the aqueous solution comprising, as the reducing saccharides, a monosaccharide as a first component and a reducing trisaccharide as a second component.

In the oxygen detector according to the present invention, more preferably, the first component further comprises a reducing disaccharide.

In the oxygen detector according to the present invention, any one or two or more of D-mannose, D-glucose, D-fructose, D-erythrose, and D-altrose are preferably used as the monosaccharide.

In the oxygen detector according to the present invention, any one or two of maltose and lactose are preferably used as the reducing disaccharide.

In the oxygen detector according to the present invention, any one or two or more of maltotriose, cellotriose, manninotriose, and panose are preferably used as the reducing trisaccharide.

The oxygen detector according to the present invention preferably further comprises a dye not reduced by the reducing saccharides.

The oxygen detector according to the present invention preferably comprises 10 parts by weight to 30 parts by weight of the reducing saccharides, 0.5 parts by weight to 2.5 parts by weight of the basic substance, and 0.01 parts by weight to 0.1 parts by weight of the redox dye when the total weight of the carrier and the oxygen indicator aqueous solution carried on the carrier is 100 parts by weight.

In the oxygen detector according to the present invention, when the basic substance is 100 parts by weight, the amount of water in the oxygen indicator aqueous solution is preferably 450 parts by weight to 1050 parts by weight.

In the oxygen detector according to the present invention, the carrier is preferably sheet-shaped.

A method for manufacturing an oxygen detector according to the present invention is a method for manufacturing an oxygen detector comprising reducing saccharides, a basic substance, and a redox dye reduced by the reducing saccharides, comprising a first step of preparing a reducing saccharide aqueous solution comprising the reducing saccharides; a second step of preparing a basic substance aqueous solution comprising the basic substance; a third step of preparing a redox dye aqueous solution comprising the redox dye; a fourth step of mixing the aqueous solution, the basic substance aqueous solution, and the redox dye aqueous solution to prepare an oxygen indicator aqueous solution; and a fifth step of allowing the oxygen indicator aqueous solution to be carried on a carrier, wherein the reducing saccharide aqueous solution comprises a monosaccharide as a first component and a reducing trisaccharide as a second component.

In the method for manufacturing an oxygen detector according to the present invention, the first component preferably further comprises a reducing disaccharide.

In the method for manufacturing an oxygen detector according to the present invention, any one or two or more of D-mannose, D-glucose, D-fructose, D-erythrose, and D-altrose are preferably used as the monosaccharide.

In the method for manufacturing an oxygen detector according to the present invention, any one or two of maltose and lactose are preferably used as the disaccharide.

In the method for manufacturing an oxygen detector according to the present invention, as the reducing trisaccharide, any one or two or more reducing trisaccharides, among maltotriose, cellotriose, manninotriose, and panose, are preferably used.

In the method for manufacturing an oxygen detector according to the present invention, the reducing saccharide aqueous solution preferably comprises 20% by weight to 40% by weight of the first component and 30% by weight to 50% by weight of the second component.

EFFECTS OF THE INVENTION

According to the oxygen indicator aqueous solution for an oxygen detector, the oxygen detector, and the method for manufacturing an oxygen detector according to the present invention, by comprising the second component comprising a reducing trisaccharide as the reducing saccharides, the reducing saccharides can be stably maintained to prevent the browning of the reducing saccharides and a decrease in reducing power, compared with the case of comprising the first component comprising a monosaccharide or a monosaccharide and a reducing disaccharide alone. Thus, the oxygen detector according to the present invention has high heat resistance. So, the oxygen detector can be stored at room temperature, and can maintain an excellent ability to detect oxygen, regardless of the atmospheric temperature. In addition, since the oxygen detector according to the present invention can be stored at room temperature, the product storage cost before shipment can be reduced. Further, it is possible to provide an oxygen detector that exhibits a clear color change and a quick color change response according to a change in the amount of oxygen in the atmosphere, even when it is used in a high temperature atmosphere, such as in summer.

DETAILED DESCRIPTION OF THE PREFERRED EMBODIMENT

A mode for implementing an oxygen detector and a method for manufacturing an oxygen detector according to the present invention will be described below.

[Mode of Oxygen Detector According to the Present Invention]

In the oxygen detector according to the present invention, an oxygen indicator aqueous solution is carried on a carrier, and a change in the amount of oxygen in the atmosphere is made visible by changing the color according to the change in the amount of oxygen in the atmosphere.

Oxygen indicator aqueous solution: First, the oxygen indicator aqueous solution will be described. The oxygen indicator aqueous solution according to the present invention is an aqueous solution comprising reducing saccharides, a basic substance, and a redox dye reduced by the reducing saccharides. In the present invention, a first component comprising a monosaccharide or a monosaccharide and a reducing disaccharide, and a second component comprising a reducing trisaccharide are used as the reducing saccharides. The reducing saccharides comprising these first component and second component are used to maintain the above redox dye in a reduced state. The use of such reducing saccharides in maintaining the redox dye in a reduced state is preferred as constituents of the oxygen detector enclosed together with food. The first component and the second component here will be described below.

In the present invention, a monosaccharide and a reducing disaccharide are used as the first component. Either of these monosaccharide and reducing disaccharide can be used alone, or these monosaccharide and reducing disaccharide can be used in combination. Here, examples of the monosaccharide can include D-mannose, D-glucose, D-fructose, D-erythrose, and D-altrose. Particularly, D-glucose is preferably used as the monosaccharide, because the D-glucose has high reducing power and easily maintains the redox dye in the reduced state. In addition, high purity D-glucose is easily available at low cost, and therefore, the cost of manufacturing the oxygen detector can be kept low.

Examples of the reducing disaccharide can include maltose and lactose. The above first component may comprise only a monosaccharide or may comprise a monosaccharide and a reducing disaccharide. When the first component comprises a monosaccharide and a reducing disaccharide, maltose comprising glucose as a constituent unit is preferred.

Next, a reducing trisaccharide is used as the second component in the present invention. Examples of this reducing trisaccharide can include maltotriose, cellotriose, manninotriose, and panose. The above second component preferably comprises any one or two or more of these reducing trisaccharides as a constituent or constituents. Particularly, maltotriose is preferably used as the reducing trisaccharide when D-glucose is used as the monosaccharide of the above first component. Maltotriose is a trisaccharide in which three glucose molecules are $\alpha$-1, 4 glycoside bonded. Glucose and maltose in which two glucose molecules are $\alpha$-1, 4 glycoside bonded, unreacted substances, may be included in commercial maltotriose. These unreacted substances can also be used as the first component as described above. Therefore, maltotriose having suitable purity can be selectively used in terms of cost, and therefore, the cost of manufacturing the oxygen detector can be kept low. When the first component comprises a monosaccharide and a reducing disaccharide, a reducing disaccharide included in a commercial reducing trisaccharide may be used.

In the oxygen indicator aqueous solution of the present invention, by comprising the second component comprising a reducing trisaccharide, together with the above first component, as the reducing saccharides, the browning of the reducing saccharides can be prevented during storage at high temperature (for example, a temperature equal to or higher than room temperature, 35° C.) to prevent a decrease in the ability to detect oxygen, compared with the case of comprising the first component alone as the reducing saccharides. Therefore, the oxygen detector manufactured using this oxygen indicator aqueous solution has excellent heat resistance, and a clear color change and a quick color change response at the time of oxygen detection can be maintained for a long period of time.

Here, in order to prevent the browning of the reducing saccharides, it is necessary to prevent the reaction of the reducing groups of the reducing saccharides with the basic substance in the oxygen indicator aqueous solution. By preventing the reaction of the reducing groups of the reducing saccharides with the basic substance, the redox dye is maintained in the reduced state, and a decrease in the ability to detect oxygen can be prevented.

When reducing saccharides form chain structures in an aqueous solution, each has one reducing group per molecule. Particularly, monosaccharides tend to be unstable in an alkaline solution, and therefore, the monosaccharides have high reactivity. On the other hand, as the number of bonds between monosaccharide molecules constituting a reducing saccharide increases, its reactivity decreases. Therefore, by using a reducing trisaccharide, the second component, in combination with the above first component, rather than using the above first component alone, the reactivity of the whole reducing saccharides can be decreased to prevent the browning of the reducing saccharides in the oxygen indicator aqueous solution. Of course, the reducing saccharides are added to the oxygen indicator aqueous solution in such an amount that the redox dye is maintained in the reduced state in an oxygen-free state.

In order to prevent the browning of the reducing saccharides, the use of a polysaccharide, instead of the above-described trisaccharide, an oligosaccharide, is also considered. However, a polysaccharide has lower reactivity and higher molecular weight than an oligosaccharide. Therefore, when a polysaccharide is used as a reducing saccharide, the amount of the reducing saccharides added, required to maintain the redox dye in the reduced state in an oxygen-free state, increases, compared with a case where a monosaccharide is used alone. As the amount of the polysaccharide added increases, the viscosity of the aqueous solution increases, and therefore, it is difficult to allow the oxygen indicator aqueous solution to be carried on a carrier. Then, by using the first component and the second component comprising a reducing trisaccharide in combination, the viscosity of the oxygen indicator aqueous solution can be kept low. In addition, by using the first component and the second component in combination, an excellent effect can be obtained which indicates that with a reducing power equal to that in a case where a monosaccharide is used alone being maintained, the browning of the reducing saccharides can be prevented to prevent a decrease in the ability to detect oxygen.

The basic substance is used to prepare the oxygen indicator aqueous solution as an alkaline solution. Examples of such a basic substance can include alkali metal compounds, specifically, hydroxides and carbonates of sodium, potassium, and the like. Among these alkali metal compounds, sodium hydroxide, potassium hydroxide, and the like are preferably used.

The redox dye is a dye that is reduced by the above reducing saccharides and reversibly changes color between an oxidized state and a reduced state. Examples of such a dye include methylene blue, new methylene blue, Lauth's violet, and methylene green. Any one or two or more of these dyes are used with the redox dye.

When a dye that is colorless in a reduced state, such as methylene blue, is used as the redox dye, a dye that is not reduced by the reducing saccharides is preferably used. It is easier to determine the presence or absence of oxygen with the naked eye by using a dye that with the redox day. Examples of such a dye can include a red food coloring, safranine T, and phenosafranine. These red food coloring, safranine T, and phenosafranine are all red dyes and are dyes that do not change color, regardless of the presence or absence of oxygen in the atmosphere.

For example, when a red dye that is not reduced by the reducing saccharides used with the methylene blue, the oxygen indicator aqueous solution changes the color, depending on the presence or absence of oxygen in the atmosphere gas, as follows. First, in the case of an oxygen-free state, the methylene blue is maintained in a reduced state by the reducing saccharides, and therefore the color of the methylene blue is colorless (leuco methylene blue). At this time, the color of the oxygen indicator aqueous solution is red due to the above red dye. On the other hand, in the case of a state in which oxygen is present, the methylene blue is oxidized, and the color of the methylene blue becomes blue. At this time, the color of the oxygen indicator aqueous solution becomes purple to blue. In this manner, when a redox dye that is colorless in a reduced state is used, a change in the color of the oxygen detector accompanying a change in the amount of oxygen is made clearer by adding a dye that is not reduced by the reducing saccharides to the oxygen indicator aqueous solution, and therefore, the presence or absence of oxygen can be visible with the naked eye.

Oxygen detector and mode of manufacturing of oxygen detector: The oxygen detector and the method for manufacturing an oxygen detector according to the present invention will be described. The oxygen detector is manufactured by preparing the above-described oxygen indicator aqueous solution and allowing this oxygen indicator aqueous solution to be carried on a carrier.

First, an example of the preparation of the oxygen indicator aqueous solution will be described. When the oxygen indicator aqueous solution is prepared, first, a reducing saccharide aqueous solution (A) comprising a predetermined concentration of the above reducing saccharides, a basic substance aqueous solution (B) comprising a predetermined concentration of the above basic substance, an aqueous solution (C) comprising a predetermined concentration of a dye not reduced by the reducing saccharides, added as required, and a redox dye aqueous solution (D) comprising a predetermined concentration of a redox dye are prepared.

Next, the reducing saccharide aqueous solution (A) and the basic substance aqueous solution (B) are mixed to prepare a reducing saccharide alkaline aqueous solution (E) adjusted to a predetermined pH. This reducing saccharide alkaline aqueous solution (E) is mixed with the aqueous solution (C) comprising a dye not reduced by the reducing saccharides, as required (F). Then, by mixing the aqueous solution ((E) or (F)) prepared in this manner and the redox dye aqueous solution (D), an oxygen indicator aqueous solution (G) according to the present invention is prepared.

Here, the aqueous solution (A) comprising the reducing saccharides used when the oxygen indicator aqueous solution is prepared (manufactured) preferably comprises 20 parts by weight (20% by weight) to 40 parts by weight (40% by weight) of the first component and 30 parts by weight (30% by weight) to 50 parts by weight (50% by weight) of the second component when the aqueous solution (A) is 100 parts by weight. By comprising the first component and the second component in the above ranges respectively in preparing the aqueous solution comprising the reducing saccharides, the browning of the reducing saccharides can be prevented, with the reducing power for the redox dye maintained, to maintain the ability to detect oxygen, compared with the case of comprising the first component alone.

Here, if the proportion of the first component is less than 30 parts by weight, sufficient reduction action on the redox dye is not obtained, which is not preferred. If the proportion of the first component is more than 50 parts by weight, the browning of the reducing saccharides tends to occur as the atmospheric temperature increases, and therefore, such a proportion is not preferred. If the proportion of the second component is less than 30 parts by weight, the browning of the monosaccharide and the reducing disaccharide tends to occur as the atmospheric temperature increases, and therefore, such a proportion is not preferred. On the other hand, if the proportion of the second component is more than 50 parts by weight, sufficient reduction action on the redox dye is not obtained, which is not preferred.

Carrier: Next, a carrier on which the oxygen indicator aqueous solution is carried will be described. The material of the carrier on which the oxygen indicator aqueous solution is carried is not particularly limited and need only be an absorber that can be impregnated with the oxygen indicator aqueous solution. For example, organic polymer materials, alkaline earth metals, silicon dioxide, and the like can be used as such a material constituting the carrier. In the present invention, particularly, organic polymer materials are preferred as the material constituting the carrier, considering the absorbency of the oxygen indicator aqueous solution, stability, and the like. Particularly, ion exchange resins or cellulose materials are preferred as the organic polymer materials. Here, ion exchange resins are insoluble and porous synthetic resins having an acidic group or a basic group capable of performing ion exchange. Bleached kraft paper is preferred as the cellulose material. A carrier comprising bleached kraft paper can maintain the oxygen indicator aqueous solution in a state preferred for the oxygen detector. In addition, since the bleached kraft paper is bleached paper, the coloration of the dye(s) included in the oxygen indicator aqueous solution, such as the redox dye, is clear. Thus, a change in color of the oxygen detector, with a change in the amount of oxygen in the atmosphere, can be clearer.

In the present invention, the shape of the carrier is also not particularly limited and can be various shapes, such as, a sheet shape, a tablet shape, and a powder shape, according to the material constituting the carrier. Particularly, a form having a sufficient surface area compared with the volume is preferred, and a form with excellent handling properties is preferred. From such viewpoints, the shape of the carrier is more preferably a sheet shape in the present invention. Since the carrier has a sufficient surface area compared with the volume, the contact surface area between the atmosphere gas and the oxygen indicator aqueous solution can be increased, and a sufficient ability to detect oxygen can be exhibited even if the oxygen detector is miniaturized.

The thickness of the carrier is preferably 200 μm or more and more preferably 200 μm to 500 μm. If the thickness of the carrier is less than 200 μm, the impregnation amount of the oxygen indicator aqueous solution is reduced, and therefore, the ability of the oxygen detector to detect oxygen decreases. If the thickness of the carrier is more than 500 μm, packaging reliability in packaging this sheet-shaped carrier in a wrapping material may be impaired.

After the oxygen indicator aqueous solution is carried on the carrier, the oxygen indicator aqueous solution is dried, to a predetermined extent, to manufacture the oxygen detector. The presence of a proper amount of water is necessary for the oxygen detector according to the present invention to detect oxygen. The water content is not particularly limited and can be appropriately changed according to the use conditions. When the water content is an amount of water that provides a concentration in which the oxidation-reduction reaction of the redox dye occurs smoothly in the presence of the reducing saccharides and the basic substance, it is preferable. In other words, preferably, the amount of water is adjusted so that the concentration of the redox dye in the oxygen indicator aqueous solution carried on the carrier is a concentration in which the oxidation-reduction reaction of the redox dye occurs smoothly in the presence of the reducing saccharides and the basic substance adjusted to predetermined amounts. Since the oxidation-reduction reaction occurs smoothly, a quick color change response and a clear color change can be ensured, and when the amount of oxygen in the atmosphere is changed, this can be immediately detected.

For example, when an alkali metal compound is used as the basic substance, such an amount of water is preferably 450 parts by weight to 1050 parts by weight, and particularly preferably 550 parts by weight to 950 parts by weight, with respect to 100 parts by weight of the alkali metal compound. When the water content is 450 parts by weight to 1050 parts by weight, it is an amount of water that can be carried on the carrier, and the oxidation-reduction reaction of the redox dye can occur smoothly in the presence of the reducing saccharides and the basic substance, as described above. Particularly, when the water content is 550 parts by weight to 950 parts by weight, the oxygen indicator aqueous solution with a concentration suitable for the oxidation reaction of the redox dye can be carried on the carrier, with the carrier being in a good state, and therefore, a quick color change response and a clear color change can be obtained at the time of oxygen detection.

In the drying, air drying, heat drying, or vacuum drying may be performed. But, in terms of improving productivity, heat drying or vacuum drying is preferably performed.

The oxygen detector manufactured in the above manner comprises 10 parts by weight to 30 parts by weight of the reducing saccharides, 0.5 parts by weight to 2.5 parts by weight of the basic substance, and 0.01 parts by weight to 0.1 parts by weight of the redox dye when the total weight is 100 parts by weight. Since the oxygen detector comprises the reducing saccharides, the basic substance, and the redox dye as solid components in such ranges, the oxidation-reduction reaction of the redox dye can occur smoothly in the presence of the reducing saccharides and the basic substance, and a quick color change response and a clear color change can be obtained at the time of oxygen detection. The above "total" weight refers to the total weight obtained by summing the weight of "the carrier" and the weight of "the oxygen indicator aqueous solution" carried on the carrier and does not include the weight of a wrapping material covering the carrier, such as a transparent film, described next, or a deoxidizer.

The oxygen detector of the present invention preferably has a configuration in which at least the surface of the carrier carrying the oxygen indicator aqueous solution is covered with a transparent film. This is because by covering the surface of the carrier with the transparent film, the oxygen indicator aqueous solution is not in contact with a substance stored, such as food, medicine, or the like, even if the oxygen detector touches the food medicine, or the like, which is hygienic.

For the transparent film used here, any transparent film having certain strength can be used. For example, a film of polyethylene, polypropylene, polyvinyl chloride, polystyrene, cellulose acetate, cellophane, or the like can be used.

In addition, the oxygen detector of the present invention may have a configuration in which the carrier carrying the oxygen indicator aqueous solution is hermetically enclosed in a flat oxygen detector bag comprising a transparent film. By hermetically enclosing the carrier carrying the oxygen indicator aqueous solution in the flat oxygen detector bag comprising a transparent film, in this manner, the oxygen detection function can be prevented from being impaired by the components of a stored substance, such as food, medicine, or the like. In other words, in a case where the carrier carrying the oxygen indicator aqueous solution is exposed or partly exposed to the outside, when the water, oil, alcohol, and the like of food or the like are present, these intrude into the carrier from the exposed portion, and the color of the oxygen indicator aqueous solution changes, and therefore, the oxygen detection function is impaired. By hermetically enclosing the carrier carrying the oxygen indicator aqueous solution in the flat oxygen detector bag comprising a transparent film to constitute the oxygen detector, such a problem does not occur.

The transparent film used here needs to be permeable to oxygen and be impermeable to liquid, such as water, oil, and alcohol. A film of polyethylene, polypropylene, polyester, polyamide, or the like can be used as such a transparent film. A film of polyester, polyamide, or the like with low oxygen permeation is preferably used by opening pinholes that are very minute to the extent of being less likely to be affected by water, alcohol, oil, and the like. More specifically, low density polyethylene (LDPE) and linear low density polyethylene (LLDPE) are preferably used as polyethylene, and cast polypropylene (CPP), biaxially oriented polypropylene (BOPP), and the like are preferably used as polypropylene. These synthetic resin films are used not only as single-layer films but also as laminated films in which films of different materials are laminated. Examples of these laminated films include two-layer films, such as OPP/CPP, OPP/LDPE, PET/LDPE, and PET/CPP, and films having three or more layers, such as LDPE/OPP/LDPE, LDPE/CPP/LDPE, and CPP/OPP/LDPE.

The oxygen detector according to the present invention may be used alone, but may be integrated with a deoxidizer for use as a composite deoxidizer. By integrating a sheet-shaped oxygen detector using a sheet-shaped carrier with a deoxidizer, the deoxidizer and the oxygen detector need not be separately enclosed and can be simultaneously enclosed when they are enclosed in the packaging container (including a packaging bag) of food or the like, and therefore, handling complicatedness is eliminated. In addition, failure to enclose either one can be prevented.

The deoxidizer used integrated with the oxygen detector according to the present invention is not particularly limited and may be an organic deoxidizer or an inorganic deoxidizer based on an iron powder as long as it functions well as a deoxidizer.

For example, sticking the oxygen detector by suitable sticking means at the desired position of a deoxidizer bag in which the deoxygenating agent is enclosed is considered as a method for integrating the oxygen detector with the deoxidizer. The sticking means is not particularly limited, and for example, a double-sided adhesive tape, an adhesive, a thickener, and the like are preferably used.

The present invention will be specifically described below by giving an Example and a Comparative Example. However, the present invention is not limited to the following Example.

[Preparation of Oxygen Indicator Aqueous Solution]

An oxygen indicator aqueous solution in an Example was prepared in the following manner.

First, 24 g of water, 24 g of glucose, and 120 g of oligosaccharides (commercial product) were mixed using a magnetic stirrer to prepare a reducing saccharide aqueous solution (A) in which reducing saccharides were dissolved in water.

In this Example, in the preparation of the reducing saccharide aqueous solution (A), commercial oligosaccharides having the following composition were used.

| Water | 25 parts by weight |
|---|---|
| Glucose (monosaccharide) | 4 parts by weight |
| Maltose (disaccharide) | 19 parts by weight |
| Maltotriose (trisaccharide) | 52 parts by weight |

The reducing saccharide aqueous solution (A) prepared in this manner comprises 31 parts by weight (31% by weight) of a first component comprising glucose and maltose, and 37 parts by weight (37% by weight) of a second component comprising maltotriose, with respect to 100 parts by weight of the reducing saccharide aqueous solution (A).

Next, 23 g of water and 7 g of sodium hydroxide as a basic substance were mixed using the magnetic stirrer to provide a basic substance aqueous solution (B).

In addition, 30 g of water and 0.1 g of a red food coloring as a dye not reduced by the reducing saccharides were mixed using the magnetic stirrer to provide a red food coloring aqueous solution (C).

Further, 30 g of water and 0.3 g of methylene blue as a redox dye were mixed using the magnetic stirrer to provide a redox dye aqueous solution (D).

Then, 137 g of the reducing saccharide aqueous solution (A) and 27 g of the basic substance aqueous solution (B) were mixed using the magnetic stirrer to prepare an aqueous solution (E) having pH adjusted to be alkaline. 27 g of the red food coloring aqueous solution (C) was added to the total amount of this alkaline aqueous solution (E), and they were mixed using the magnetic stirrer to prepare an aqueous solution (F) to which the red food coloring was added. Then, 32 g of this aqueous solution (F) and 4 g of the redox dye aqueous solution (D) were mixed using the magnetic stirrer to prepare an oxygen indicator aqueous solution (G).

The oxygen indicator aqueous solution (G) prepared by the above steps comprised 18.8 g (52.2 parts by weight) of water, 4.1 g (11.4 parts by weight) of glucose, 3.2 g (8.9 parts by weight) of maltose, 8.8 g (24.4 parts by weight) of maltotriose, 1.0 g (2.8 parts by weight) of sodium hydroxide, 0.02 g (0.06 parts by weight) of the red food coloring, and 0.04 g (0.1 parts by weight) of methylene blue. In this case, when the total weight (17.16 g) of various components (solid components: glucose, maltose, maltotriose, sodium hydroxide, the red food coloring, and methylene blue) dissolved in water, the solvent, was 100 parts by weight, the glucose was 23.9 parts by weight, the maltose was 18.6 parts by weight, the maltotriose was 51.3 parts by weight (the total amount of the reducing saccharides was 93.8 parts by weight), the sodium hydroxide was 5.8 parts by weight, the red food coloring was 0.1 parts by weight, and the methylene blue was 0.2 parts by weight.

[Manufacturing of Oxygen Detector]

Next, a filter paper having a width of 15 mm and a length of 50 mm was impregnated with the oxygen indicator aqueous solution (G) prepared by the above steps and dried at 35° C. for 3 hours to fabricate an oxygen detector A. At this time, the color of the oxygen detector A was blue. In addition, the oxygen detector A manufactured in this manner comprised 19.0 parts by weight of the reducing saccharides (4.7 parts by weight of glucose, 3.9 parts by weight of maltose, and 10.4 parts by weight of maltotriose), 1.3 parts by weight of sodium hydroxide as the basic substance, 0.02 parts by weight of the red food coloring, and 0.05 parts by weight of methylene blue, the redox dye, when the total weight (the weight obtained by summing the weight of the filter paper, and the weight of the oxygen indicator aqueous solution G with which the filter paper was impregnated, after the drying) was 100 parts by weight. In addition, quantitative analysis was performed on the oxygen detector A manufactured in this manner by a differential refractive index detector Shodex RI-101 manufactured by Showa Denko K.K., using a sugar analysis column KS-801 manufactured by Showa Denko K.K., at a column temperature of 60° C., using water as the mobile phase. As a result, when the total weight of various components (solid components: glucose, maltose, maltotriose, sodium hydroxide, the red food coloring, and methylene blue) dissolved in the oxygen indicator aqueous solution G carried on the carrier was 100 parts by weight, 23.2 parts by weight of glucose, 19.0 parts by weight of maltose, and 51.1 parts by weight of maltotriose, 6.4 parts by weight of sodium hydroxide as the basic substance, 0.08 parts by weight of the red food coloring, and 0.25 parts by weight of methylene blue, the redox dye, were included. For the weight of the various components per unit area of the filter paper, 1.20 mg/m$^2$ of glucose, 0.98 mg/m$^2$ of maltose, 2.64 mg/m$^2$ of maltotriose, 0.33 mg/m$^2$ of sodium hydroxide, 0.004 mg/m$^2$ of the red food coloring, and 0.013 mg/m$^2$ of methylene blue were included, and 5.17 mg/m$^2$ of the solid components were included per unit area of the filter paper.

Comparative Example

[Preparation of Oxygen Indicator Aqueous Solution]

An oxygen indicator aqueous solution in a Comparative Example was prepared in the following manner.

72 g of water and 72 g of glucose were mixed using the magnetic stirrer to prepare a reducing saccharide aqueous solution (A') in which only a monosaccharide as a reducing saccharide was dissolved in water. 50 parts by weight (50% by weight) of the monosaccharide was included in 100 parts by weight of this reducing saccharide aqueous solution (A').

Then, the basic substance solution (B), the red food coloring aqueous solution (C), and the redox dye aqueous solution (D) were prepared by the same methods as in the Example.

Then, the reducing saccharide aqueous solution (A'), the basic substance aqueous solution (B), the red food coloring aqueous solution (C), and the redox dye aqueous solution (D) were mixed by the same method as in the Example described above, except that the above reducing saccharide aqueous solution (A') was used instead of the reducing saccharide aqueous solution (A), to prepare an oxygen indicator aqueous solution (G') as the Comparative Example.

The oxygen indicator aqueous solution (G') prepared by the above steps comprised 23.5 g (65.0% by weight) of water, 11.5 g (31.8% by weight) of glucose, 1.1 g (3.0% by weight) of sodium hydroxide, 0.02 g (0.06% by weight) of the red food coloring, and 0.04 g (0.11% by weight) of methylene blue. In this case, when the total weight (12.66 g) of various components (solid components: glucose, sodium hydroxide, the red food coloring, and methylene blue) dissolved in water, the solvent, was 100 parts by weight, the glucose was 90.8 parts by weight, the sodium hydroxide was 8.7 parts by weight, the red food coloring was 0.16 parts by weight, and the methylene blue was 0.32 parts by weight.

[Manufacturing of Oxygen Detector]

An oxygen detector A' was fabricated by the same method as in the Example, except that the oxygen indicator aqueous solution (G') prepared in the above manner was used. At this time, the color of the oxygen detector A' was blue as in the Example. In addition, the oxygen detector A' manufactured in this manner comprised 18.5 parts by weight of glucose as the reducing saccharide, 1.8 parts by weight of sodium hydroxide as the basic substance, 0.04 parts by weight of the red food coloring, and 0.08 parts by weight of methylene blue, the redox dye, when the total (the weight obtained by summing the weight of the filter paper, and the weight of the oxygen indicator aqueous solution G' with which the filter paper was impregnated, after the drying) was 100 parts by weight. In addition, quantitative analysis was performed on the oxygen detector A' manufactured in this manner by the differential refractive index detector Shodex RI-101 manufactured by Showa Denko K.K., using the sugar analysis column KS-801 manufactured by Showa Denko K.K., at a column temperature of 60° C., using water as the mobile phase, as in the Example. As a result, when the total weight of various components (solid components: glucose, sodium hydroxide, the red food coloring, and methylene blue) dissolved in the oxygen indicator aqueous solution G' carried on the carrier was 100 parts by weight, 90.7 parts by weight of glucose, 8.7 parts by weight of sodium hydroxide as the basic substance, 0.2 parts by weight of the red food coloring, and 0.4 parts by weight of methylene blue, the redox dye, were included. For the weight of the various components per unit area of the filter paper, 4.69 mg/m$^2$ of glucose, 0.45 mg/m$^2$ of sodium hydroxide, 0.01 mg/m$^2$ of the red food coloring, and 0.02 mg/m$^2$ of methylene blue were included, and 5.17 mg/m$^2$ of the solid components were included per unit area of the filter paper.

[Evaluation Results]

1. Evaluation Regarding Change in Color Depending on Storage Temperature

First, evaluation regarding a change in color depending on storage temperature was performed. In performing the evaluation, first, the oxygen detector A obtained in the Example, and the oxygen detector A' obtained in the Comparative Example were stored in an oxygen-free atmosphere to bring the redox dye to a reduced state under the action of the reducing saccharide(s). Specifically, two KNY (vinylidene-coated nylon)/PE bags having an oxygen permeability of 10 ml/m$^2$·day in which one oxygen detector A was sealed together with a deoxidizer were fabricated to provide one as sample 1-1 and the other as sample 1-2.

Similarly, two KNY (vinylidene-coated nylon)/PE bags having an oxygen permeability of 10 ml/m$^2$·day in which one sheet of the oxygen detector A' was sealed together with a deoxidizer were fabricated to provide one as sample 2-1 and the other as sample 2-2. Each of the samples fabricated in this manner (the sample 1-1 to the sample 2-2) was stored in a thermostat bath at 25° C., and the atmosphere of the oxygen detectors A and the oxygen detectors A' was brought to an oxygen-free state by the deoxidizers. After a lapse of 24 hours, for the samples (the sample 1-1 to the sample 2-2), the color of the oxygen detectors A and the oxygen detectors A' was visually identified. The color of each the oxidant detector was red.

Next, the sample 1-1 and the sample 2-1 were stored in a thermostat bath at 10° C., and the sample 1-2 and the sample 2-2 were stored in a thermostat bath at 35° C. For the samples, the color of the oxygen detectors A and the oxygen detectors A' was measured by a colorimeter ZE-2000 manufactured by Nippon Denshoku Industries Co., Ltd. for each 10 days. The measured values (L values, a values, b values, and ΔE values) are shown in Table 1. In Table 1, as the color difference values, values with reference to the sample 1-1 are shown for the Example, and values with reference to the sample 2-1 are shown for the Comparative Example.

TABLE 1

| | | Example (oxygen detector A) | | Comparative Example (oxygen detector A') | |
|---|---|---|---|---|---|
| | | Sample 1-1 (stored at 10° C.) | Sample 1-2 (35° C.) | Sample 2-1 (10° C.) | Sample 2-2 (35° C.) |
| Baseline | L value | 60.12 | 59.73 | 66.79 | 69.66 |
| | a value | 26.35 | 28.78 | 23.66 | 21.27 |
| | b value | −16.13 | −18.88 | −19.68 | −17.92 |
| | ΔE | — | 3.67 | — | 4.13 |
| 10 days | L value | 59.04 | 59.73 | 65.74 | 66.07 |
| | a value | 26.70 | 28.90 | 25.25 | 21.22 |
| | b value | −14.77 | 4.07 | −19.80 | 10.55 |
| | ΔE | — | 18.29 | — | 30.62 |
| 20 days | L value | 58.55 | 60.10 | 66.24 | 64.06 |
| | a value | 26.16 | 27.46 | 27.33 | 20.12 |
| | b value | −12.45 | 5.12 | −18.15 | 16.00 |
| | ΔE | — | 17.70 | — | 34.97 |
| 30 days | L value | 58.25 | 59.40 | 66.68 | 63.49 |
| | a value | 27.25 | 26.80 | 28.95 | 18.52 |
| | b value | −10.76 | 4.84 | −16.52 | 16.78 |
| | ΔE | — | 15.64 | — | 35.05 |

As shown in Table 1, after 30 days passed, for the oxygen detectors A fabricated in the Example, the color difference value (ΔE) between the sample 1-1 stored at 10° C. and the sample 1-2 stored at 35° C. was 15.64, with reference to the sample 1-1. On the other hand, for the oxygen detectors A' fabricated in the Comparative Example, the color difference value (ΔE) between the sample 2-1 stored at 10° C. and the sample 2-2 stored at 35° C. was 35.05, with reference to the sample 2-1. From the results, it is seen that in the oxygen detectors A fabricated in the Example, by using the monosaccharide in combination with the trisaccharide, as the reducing saccharides, rather than using the monosaccharide alone, degradation in color was prevented, and heat resistance was excellent, compared with the Comparative Example using the monosaccharide alone. It is considered that this was because by using together the first component comprising the monosaccharide and the disaccharide, and the second component comprising the trisaccharide, as the reducing saccharides, as described above, the reaction of the reducing groups of the reducing saccharides with the basic substance was decreased, even if the oxygen detectors A were stored at high temperature (35° C. in the Example), compared with the case of using the monosaccharide alone. It is considered that by decreasing the reaction, it was possible to decrease the browning of the reducing saccharides and maintain the redox dye stably in the reduced state. It is considered that as a result, the oxygen detectors A were prevented from turning brown due to the browning of the reducing saccharides. From these, it was confirmed that for the oxygen detectors A in the Example, there was no degradation in color, even after the storage at high temperature for 30 days.

2. Evaluation Regarding Color Change Speed Depending on Storage Temperature

Next, evaluation regarding color change speed depending on storage temperature was performed. The evaluation was performed using the above sample 1-1, sample 1-2, sample 2-1, and sample 2-2. The samples were stored at respective storage temperatures for 30 days. After 30 days passed, the bags were opened, and the oxygen detectors A and the oxygen detectors A' were removed. At this time, the oxygen detectors A and the oxygen detectors A' all changed to a purple to blue color.

Then, each of these oxygen detectors A (the sample 1-1 and the sample 1-2) and oxygen detectors A' (the sample 2-1 and the sample 2-2) changing to the purple to blue color was sealed, together with a deoxidizer, in a KNY/PE bag having an oxygen permeability of 10 ml/m²·day, and stored in a thermostat bath at 25° C. Then, after 24 hours passed, the oxygen concentration in each bag was measured by an oxygen analyzer manufactured by Toray Engineering Co., Ltd. As a result, the oxygen concentration in each bag was 0.1%. Then, the time required for the oxygen detectors A and the oxygen detectors A' to change from the purple or blue color to a red color was measured, with reference to a point of time when the oxygen concentration in each bag reached 0.1% (a point of time after 24 hours passed). The results are shown in Table 2.

TABLE 2

| | Example (oxygen detector A) | | Comparative Example (oxygen detector A') | |
|---|---|---|---|---|
| | Sample 1-1 (10° C.) | Sample 1-2 (35° C.) | Sample 2-1 (10° C.) | Sample 2-2 (35° C.) |
| Time required for color change (25° C.) | 8 hours | 8 hours | 8 hours | No color change |

As is seen from Table 2, the oxygen detector A changed to a red color in 8 hours, both when it was stored at 10° C. for 30 days, and when it was stored at 35° C. for 30 days. From this, it is seen that even when the oxygen detector A was stored at high temperature, the redox dye was reduced by the reducing saccharides, and the ability of the oxygen detector A to detect oxygen was maintained.

On the other hand, when the oxygen detector A' was stored at low temperature, the oxygen detector A' changed to a red color in 8 hours as in the oxygen detector A fabricated in the Example, and therefore, it can be confirmed that the ability of the oxygen detector A' to detect oxygen was maintained during the low temperature storage. But, it is seen that when the oxygen detector A' was stored at 35° C. for 30 days, the oxygen detector A' did not change to a red color, and the redox dye did not return to the reduced state. It is considered that this was because while the oxygen detector A' was stored at high temperature, the reducing groups of the reducing saccharide reacted with the basic substance and decomposed, and therefore, reduction action on the redox dye was not exerted.

In addition, to maintain the redox dye in the reduced state in an oxygen-free state, the content of the reducing saccharides is high in this Example, compared with the case shown in the Comparative Example using glucose, a monosaccharide, alone. As a result, when the oxygen indicator aqueous solution in this Example and the oxygen indicator aqueous solution in the Comparative Example having the same weight are compared, the concentration of the redox dye to water in the oxygen indicator aqueous solution in this Example is higher than that of the Comparative Example. Therefore, the oxygen indicator aqueous solution according to the present invention can be prepared as a higher concentration redox dye aqueous solution than conventional ones. Therefore, the oxygen detector in this Example can exhibit a clear color change and a quick color change response according to a change in the amount of oxygen in the atmosphere due to the oxidation-reduction reaction of a high concentration of the redox dye, with the browning of the reducing saccharides prevented.

In the above manner, in the oxygen detector and the oxygen indicator aqueous solution according to the present invention, by comprising the second component comprising a reducing trisaccharide as the reducing saccharides, the reducing saccharides can be stably maintained to prevent the browning of the reducing saccharides and a decrease in reducing power, compared with the case of comprising the first component comprising a monosaccharide or a monosaccharide and a reducing disaccharide alone. In addition, the concentration of the redox dye to water can be higher than that of conventional ones. Because of these, the oxygen detector according to the present invention has high heat resistance, can be stored at room temperature, and can maintain an excellent ability to detect oxygen, regardless of the atmospheric temperature. Since the oxygen detector according to the present invention can be stored at room temperature, the product storage cost before shipment can be reduced. In addition, it is possible to provide an oxygen detector that exhibits a clear color change and a quick color change response according to a change in the amount of oxygen in the atmosphere, even when it is used in a high temperature atmosphere, such as in summer. Further, according to the method for manufacturing an oxygen detector according to the present invention, it is possible to manufacture an oxygen detector that has high heat resistance, can be stored at room temperature, and can maintain an excellent ability to detect oxygen, regardless of the atmospheric temperature, in this manner.

According to the oxygen detector and the method for manufacturing an oxygen detector according to the present invention, by comprising the second component comprising a reducing trisaccharide as the reducing saccharides, the reducing saccharides can be stably maintained to prevent the browning of the reducing saccharides and a decrease in reducing power, compared with the case of comprising the first component comprising a monosaccharide or a monosaccharide and a reducing disaccharide alone. Thus, the oxygen detector according to the present invention has high heat resistance and can be stored at room temperature. In addition, the oxygen detector according to the present invention can maintain an excellent ability to detect oxygen, regardless of the atmospheric temperature. In addition, since the oxygen detector according to the present invention can be stored at room temperature, the product storage cost before shipment can be reduced. Further, it is possible to provide an oxygen detector that exhibits a clear color change and a quick color change response according to a change in the amount of oxygen in the atmosphere, even when it is used in a high temperature atmosphere, such as in summer.

What is claimed is:

1. An oxygen detector comprising an oxygen indicator aqueous solution comprising reducing saccharides, a basic substance, and a redox dye reduced by the reducing saccharides, carried on a carrier,
    the aqueous solution comprising, as the reducing saccharides, a monosaccharide as a first component and a reducing trisaccharide as a second component,
    wherein the aqueous solution comprises 20% by weight to 40% by weight of the first component and 30% by weight to 50% by weight of the second component.

2. The oxygen detector according to claim 1, wherein the first component further comprises a reducing disaccharide.

3. The oxygen detector according to claim 2, wherein any one or two of maltose and lactose are used as the reducing disaccharide.

4. The oxygen detector according to claim 1, wherein any one or two or more of D-mannose, D-glucose, D-fructose, D-erythrose, and D-altrose are used as the monosaccharide.

5. The oxygen detector according to claim 1, wherein as the reducing trisaccharide, any one or two or more reducing trisaccharides, among maltotriose, cellotriose, manninotriose, and panose, are used.

6. The oxygen detector according to claim 1, further comprising a dye not reduced by the reducing saccharides.

7. The oxygen detector according to claim 1, comprising 10 parts by weight to 30 parts by weight of the reducing saccharides, 0.5 parts by weight to 2.5 parts by weight of the basic substance, and 0.01 parts by weight to 0.1 parts by weight of the redox dye when the total weight of the carrier and the oxygen indicator aqueous solution carried on the carrier is 100 parts by weight.

8. The oxygen detector according to claim 1, wherein the amount of water in the oxygen indicator aqueous solution is 450 parts by weight to 1050 parts by weight when the basic substance is 100 parts by weight.

9. The oxygen detector according to claim 1, wherein the carrier is sheet-shaped.

10. A method for manufacturing an oxygen detector comprising reducing saccharides, a basic substance, and a redox dye reduced by the reducing saccharides, comprising:
    preparing a reducing saccharide aqueous solution comprising the reducing saccharides;
    preparing a basic substance aqueous solution comprising the basic substance;
    preparing a redox dye aqueous solution comprising the redox dye;
    mixing the reducing saccharide aqueous solution, the basic substance aqueous solution, and the redox dye aqueous solution to prepare an oxygen indicator aqueous solution; and
    allowing the oxygen indicator aqueous solution to be carried on a carrier,
    the reducing saccharide aqueous solution comprising a monosaccharide as a first component and a reducing trisaccharide as a second component, and
    wherein the reducing saccharide aqueous solution comprises 20% by weight to 40% by weight of the first component and 30% by weight to 50% by weight of the second component.

11. The method for manufacturing an oxygen detector according to claim 10, wherein the first component further comprises a reducing disaccharide.

12. The method for manufacturing an oxygen detector according to claim 11, wherein maltose or lactose or maltose and lactose are used as the reducing disaccharide.

13. The method for manufacturing an oxygen detector according to claim 10, wherein any one or two or more of D-mannose, D-glucose, D-fructose, D-erythrose, and D-altrose are used as the monosaccharide.

14. The method for manufacturing an oxygen detector according to claim 10, wherein as the reducing trisaccharide, any one or two or more reducing trisaccharides, among maltotriose, cellotriose, manninotriose, and panose, are used.

* * * * *